(12) United States Patent
Liu et al.

(10) Patent No.: US 12,357,975 B2
(45) Date of Patent: Jul. 15, 2025

(54) CATALYST FOR PRODUCING ISOPROPYLBENZENE AND THE PRODUCTION METHOD AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Zhongneng Liu, Shanghai (CN); Duo Zhao, Shanghai (CN); Yuhao Lv, Shanghai (CN); Wendi Ma, Shanghai (CN); Guoyao Gu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 253 days.

(21) Appl. No.: 17/764,366

(22) PCT Filed: Sep. 29, 2020

(86) PCT No.: PCT/CN2020/118672
§ 371 (c)(1),
(2) Date: Mar. 28, 2022

(87) PCT Pub. No.: WO2021/058019
PCT Pub. Date: Apr. 1, 2021

(65) Prior Publication Data
US 2022/0331785 A1   Oct. 20, 2022

(30) Foreign Application Priority Data
Sep. 29, 2019 (CN) .......................... 201910930321.4
Oct. 17, 2019 (CN) .......................... 201910987687.5

(51) Int. Cl.
*B01J 23/44* (2006.01)
*B01J 21/04* (2006.01)
(Continued)

(52) U.S. Cl.
CPC .......... *B01J 23/8926* (2013.01); *B01J 23/44* (2013.01); *B01J 23/892* (2013.01); *B01J 27/16* (2013.01);
(Continued)

(58) Field of Classification Search
CPC . B01J 23/44; B01J 23/60; B01J 23/626; B01J 23/89; B01J 23/8913; B01J 23/892;
(Continued)

(56) References Cited

U.S. PATENT DOCUMENTS 6,646,139 B2    11/2003  Seo et al.
9,328,039 B2 *   5/2016  Diehl .................... B01J 23/755
(Continued)

FOREIGN PATENT DOCUMENTS

CN        1732139 A    2/2006
CN        1860087 A    11/2006
(Continued)

OTHER PUBLICATIONS

Office Action (First Office Action) issued on Dec. 19, 2023, by the Japanese Patent Office in corresponding Japanese Patent Application No. 2022-519509, and an English Translation of the Office Action. (7 pages).

(Continued)

*Primary Examiner* — Youngsul Jeong
*Assistant Examiner* — Jason Y Chong
(74) *Attorney, Agent, or Firm* — Panitch Schwarze Belsario & Nadel LLP

(57) ABSTRACT

Described are a catalyst for producing isopropylbenzene and the production method and use thereof. The catalyst includes a support and an active component supported on the support, wherein the support comprises a support substrate and a modifying auxiliary component supported on the support (Continued)

substrate, wherein the active component includes metal palladium and/or an oxide thereof, and the modifying auxiliary component is phosphorus and/or an oxide thereof; optionally, the active component further includes metal copper and/or an oxide thereof; the catalyst further includes a sulfur-containing compound.

21 Claims, 1 Drawing Sheet

(51) Int. Cl.
| | |
|---|---|
| *B01J 23/89* | (2006.01) |
| *B01J 27/16* | (2006.01) |
| *B01J 27/182* | (2006.01) |
| *B01J 31/02* | (2006.01) |
| *B01J 31/28* | (2006.01) |
| *B01J 37/02* | (2006.01) |
| *B01J 37/03* | (2006.01) |
| *B01J 37/04* | (2006.01) |
| *B01J 37/08* | (2006.01) |
| *B01J 37/18* | (2006.01) |
| *C07C 1/22* | (2006.01) |
| *C07C 1/24* | (2006.01) |

(52) U.S. Cl.
CPC ......... *B01J 27/182* (2013.01); *B01J 31/0221* (2013.01); *B01J 31/28* (2013.01); *B01J 37/0217* (2013.01); *B01J 37/0219* (2013.01); *B01J 37/0228* (2013.01); *B01J 37/0236* (2013.01); *B01J 37/0244* (2013.01); *B01J 37/031* (2013.01); *B01J 37/04* (2013.01); *B01J 37/08* (2013.01); *B01J 37/18* (2013.01); *C07C 1/22* (2013.01); *B01J 2231/643* (2013.01); *B01J 2531/005* (2013.01); *C07C 2523/44* (2013.01); *C07C 2523/72* (2013.01); *C07C 2523/755* (2013.01); *C07C 2523/89* (2013.01); *C07C 2527/18* (2013.01); *C07C 2527/182* (2013.01)

(58) Field of Classification Search
CPC ...... B01J 23/8926; B01J 27/16; B01J 27/182; B01J 27/1856; B01J 31/0221; B01J 31/28; B01J 37/0201; B01J 37/0207; B01J 37/0217; B01J 37/0219; B01J 37/0228; B01J 37/0236; B01J 37/0244; B01J 37/031; B01J 37/04; B01J 37/08; B01J 37/18; B01J 37/20; B01J 2531/005; B01J 2531/643; B01J 35/394; B01J 35/60; B01J 35/615; B01J 35/647; B01J 21/04; C07C 1/22; C07C 2523/44; C07C 2523/60; C07C 2523/62; C07C 2523/72; C07C 2523/755; C07C 2523/89; C07C 2527/18; C07C 2527/182; C07C 15/085; Y02P 20/52

See application file for complete search history.

(56) References Cited

U.S. PATENT DOCUMENTS

| | | |
|---|---|---|
| 2006/0135830 A1 | 6/2006 | Birkhoff et al. |
| 2006/0217566 A1 | 9/2006 | Suzuki et al. |
| 2018/0369788 A1 | 12/2018 | Liu et al. |

FOREIGN PATENT DOCUMENTS

| | | | |
|---|---|---|---|
| CN | 101733093 A | | 6/2010 |
| CN | 102451675 A | * | 5/2012 |
| CN | 103071495 A | * | 5/2013 |
| CN | 104151129 A | | 11/2014 |
| CN | 104230640 A | | 12/2014 |
| CN | 104230641 A | | 12/2014 |
| CN | 104151129 B | * | 3/2017 |
| CN | 107189812 A | | 9/2017 |
| CN | 110075857 A | | 8/2019 |
| JP | 2006-176492 A | | 7/2006 |
| JP | 2019-005746 A | | 1/2019 |

OTHER PUBLICATIONS

Extended European Search Report issued Sep. 22, 2023, by the European Patent Office in corresponding European Patent Application No. 20869646.8. (8 pages).
International Search Report (PCT/ISA/210) with an English translation, and Written Opinion (PCT/ISA/237) mailed on Jan. 4, 2021, by the China National Intellectual Property Administration as the International Searching Authority for International Application No. PCT/CN2020/118672. (12 pages).
"To find out who's where, look in who's who", European Chemical News, vol. 74, No. 19475-11, pp. 19-20, Mar. 2001.
First Written Opinion and Search Report issued on Jan. 30, 2023, by the Intellectual Property Office of Singapore in corresponding Singaporean Patent Application No. 11202203019R. (8 pages).
Office Action issued on Jun. 28, 2023, by the Indian Intellectual Property Office in counterpart Indian Patent Application No. 202247024210 (6 pages).
Second Office Action (Notice of Reasons for Refusal) issued on Jun. 11, 2024, by the Japanese Patent Office in corresponding Japanese Patent Application No. 2022-519509 and an English Translation of the Office Action (7 pages).
Office Action issued on Oct. 22, 2024, by the Brazilian Intellectual Property Office in corresponding BR Application No. 112022005733-4, and informal English translation of the Office Action (5 pages).
Office Action issued on Nov. 20, 2024, by the Saudi Authority for Intellectual Property Office in corresponding SA Application No. 522432091, and English translation of the Office Action (14 pages).

* cited by examiner

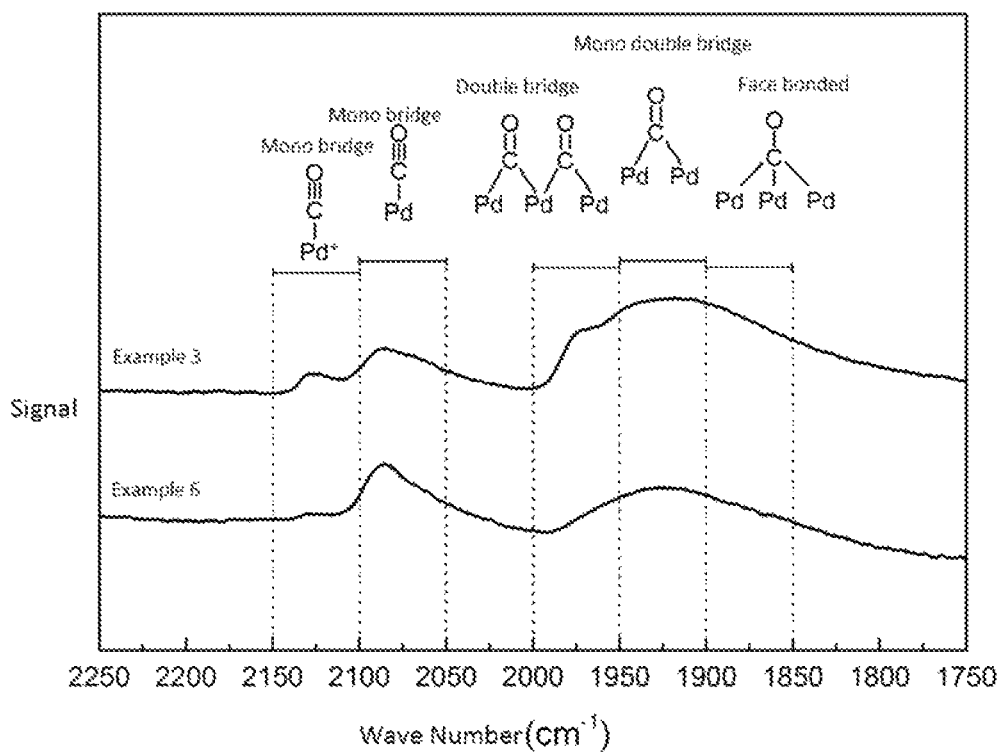

CATALYST FOR PRODUCING ISOPROPYLBENZENE AND THE PRODUCTION METHOD AND USE THEREOF

TECHNICAL FIELD

This invention relates to a catalyst for producing isopropylbenzene, in particular, to a catalyst for producing isopropylbenzene by using α,α-dimethylbenzyl alcohol (DMBA), and the production method and use thereof.

BACKGROUND ART

Propylene oxide (PO for short) is an important organic industrial chemical material which is mainly used for producing polyether polyols, propylene glycols, propanediol ethers, etc., wherein the consumption of polyether polyols accounts for about 70%. At present, commercialized processes for the production of PO mainly include chlorohydrin process, co-oxidation process (PO/SM) and isopropylbenzene hydroperoxide recycling process (CHP). The CHP process has the following advantages: the conversion and the selectivity of the whole process are very high; the process leads to the only product of PO and is not affected by the price fluctuation of by-product of styrene, as can bring more stable economic benefits to manufacturers; the technological process is relatively simple, where the fixed investment is two thirds as much as that of the PO/SM process. Furthermore the requirements for anti-corrosion on devices in the CHP process are relatively low. In the technique for the production of propylene oxide by CHP process, a large amount of α,α-dimethylbenzyl alcohol (DMBA) is generated in the process of propylene epoxidation. The α,α-dimethylbenzyl alcohol needs to be hydrogenated to produce isopropylbenzene to re-participate in the reaction cycle.

U.S. Pat. No. 6,646,139B2 provides a process for producing isopropylbenzene by the catalytic hydrogenolysis of α,α-dimethylbenzyl alcohol with $H_2$ as a hydrogen source and copper-Cr as a catalyst. Although the conversion of α,α-dimethylbenzyl alcohol can be up to 99%, the selectivity is less than 98%. Moreover, the use of element Cr in the production of the catalyst results in a serious environmental pollution. Chinese patent CN101733093 B reported that the reaction of alumina-supported or zeolite-supported metal palladium or a mixture of palladium and Pt at a reaction temperature lower than 160° C. achieved a conversion of α,α-dimethylbenzyl alcohol greater than 99.5% and a selectivity of isopropylbenzene greater than 99.5%. The stronger acidity of the support in the patent significantly led to the polymerization of methylstyrene—an intermediate product of dehydration of α,α-dimethylbenzyl alcohol. The patent does not mention the technical problem of stability of the catalyst. Chinese patent application CN104230640 A points out that use of a palladium/$SiO_2$ catalyst can realize 100% conversion of α,α-dimethylbenzyl alcohol but a selectivity of isopropylbenzene lower than 98.5% under reaction temperature of 180° C.

A well-known method for producing isopropylbenzene is dehydrating cumyl alcohol to alpha-methyl styrene in the presence of a dehydration catalyst, and hydrogenating the alpha-methyl styrene to cumene in the presence of a hydrogenation catalyst (for example, European Chemical News Volume 74 Number 19475-11 March 2001). Chinese patent CN1732139A discloses providing cumyl alcohol and hydrogen to a dehydration catalyst to obtain a mixture comprising the resultant alpha-methyl styrene and water and hydrogen; providing the mixture to a hydrogenation catalyst, wherein the reaction temperature and pressure are so selected that the water contained in the α-methylstyrene solution after dehydration is not agglutinated. The reaction temperature is preferably 150 to 300° C., and the reaction pressure is preferably 100 to 2000 kPa. When the temperature is lower than 150° C. and the pressure is higher than 2000 kPa, water agglutination sometimes occurs at the dehydration reaction outlet, which degrades the performance of the hydrogenation catalyst. However, the well-known method cannot meet the requirements of low-cost and efficient production of isopropylbenzene.

In the prior art, there are problems including the catalyst activity and selectivity needed to be further improved, the poor stability and the serious environmental pollution in the production of isopropylbenzene by catalyzing the dehydration and hydrogenation of α,α-dimethylbenzyl alcohol.

CONTENTS OF INVENTION

The present invention provides a highly active and highly selective supported palladium catalyst having an excellent catalytic activity and selectivity, an excellent hydration resistance and a good stability in order to solve the technical problems of low activity and selectivity, poor stability and serious environmental pollution of catalysts in the prior art.

One object of the present invention is to provide a catalyst for producing isopropylbenzene, in particular, a catalyst for producing isopropylbenzene from α,α-dimethylbenzyl alcohol, comprising a support and an active component supported on the support, wherein the support comprises a support substrate and a modifying auxiliary component supported on the support substrate, wherein the active component includes metal palladium and/or oxides thereof, and the modifying auxiliary component includes phosphorus and/or oxides thereof.

The support substrate herein is not particularly limited and can be a common catalyst support in this field, unless otherwise specified. In a preferred embodiment, the support substrate is at least one selected from the group consisting of silica, alumina and activated carbon, preferably alumina.

In a preferred embodiment, the support substrate has a pore size of 10-25 nm and a specific surface area of 50-180 $m^2/g$; more preferably, the support substrate has a pore size of 12-18 nm and a specific surface area of 120-160 $m^2/g$.

In a preferred embodiment, the content of the metal palladium and/or oxides thereof in the catalyst is 0.01-5 wt %. In a further preferred embodiment, the content of the metal palladium and/or oxides thereof in the catalyst is 0.05-1 wt %, for example, 0.05-0.5 wt %, wherein the content of the metal palladium and/or oxides thereof is based on the content of element palladium therein.

In the present invention, the source of the metal palladium is not particularly limited, preferably but not limited to at least one selected from the group consisting of palladium chloride, palladium nitrate and chloropalladic acid.

In a preferred embodiment, the catalyst has a palladium dispersity of 5-10%, preferably 6.5-8.5%.

Here, the hydrogenolysis of α,α-dimethylbenzyl alcohol is the coupling of two steps of dehydration and hydrogenation. Studies have found that dehydration is the determining step of the reaction. Therefore, we should first improve the dehydration activity of the catalyst in the regulation of the catalyst, so as to improve the reaction rate of the whole reaction. The dispersity of metal palladium has a certain relationship with its grain size. Generally, the larger the grain is, the lower the dispersity is. Studies also have found that the Pd dispersity is not in a linear relationship with the grain size because TEM analysis found that the grain size of Pd did not increase significantly on a catalyst having a reduced dispersity. In addition, an appropriate grain growth of a Pd catalyst is helpful to improve the reaction selectivity. Therefore, it is necessary to control the dispersity within a reasonable range.

The dispersity of metal Pd is determined by hydrogen-oxygen titration method. The specific analysis steps include: raising the temperature of the catalyst to 120° C. (heating rate 10° C./min) in a certain hydrogen flow, the temperature retaining constant for 2 hours; then raising the temperature to 145° C., purging with argon for 1 hour and then lowering the temperature to room temperature (in argon atmosphere). Chemical adsorption of oxygen: at the room temperature, introducing oxygen by pulse to a sample tube until saturation; then purging with argon for 40 min. The determination of the amount of hydrogen titration: quantitative pulse of hydrogen is made with a six-way feeding valve (quantitative tube volume of 0.3 mL). The amount of consumed hydrogen can be calculated based on the area difference between the front and rear peaks on the chromatographic instrument, so that the dispersity of metal Pd on the catalyst can be calculated.

In a preferred embodiment, the active component further includes an active auxiliary metal and/or oxides thereof. Preferably, the active auxiliary metal is at least one selected from the group consisting of metal copper, metal zinc, metal cobalt, metal tin, metal nickel and metal silver, for example, metal copper. In a further preferred embodiment, the content of the active auxiliary metal and/or oxides thereof in the catalyst is 0.0001-0.2 wt %, preferably 0.0007-0.2 wt %, wherein the content of the active auxiliary metal and/or oxides thereof is based on the content of the auxiliary metal element therein.

In the present invention, the source of the active auxiliary metal is not particularly limited, for example but not limited to at least one selected from the group consisting of active auxiliary metal chlorides, compounds of active auxiliary metal nitrates and compounds of active auxiliary metal acetates, etc.

A Pd-based bimetallic/polymetallic catalyst modified with an active auxiliary metal (for example, Cu) can improve the selectivity of isopropylbenzene of the catalyst, particularly in the initial stage. Preferably, the Pd content by weight in the catalyst is greater than that of the active auxiliary metal (for example, Cu). That is, the ratio by weight of Pd to the active auxiliary metal (for example, Cu) is >1.

In a preferred embodiment, the content of the modifying auxiliary component (phosphorus and/or oxides thereof) in the catalyst is 0.2-20 wt %. In a further preferred embodiment, the content of the modifying auxiliary component (phosphorus and/or oxides thereof) in the catalyst is 1-15 wt %, more preferably 1-7 wt %, wherein the content of phosphorus and/or oxides thereof is based on the content of element phosphorus therein.

The source of phosphorus in the present invention is not particularly limited, preferably but not limited to at least one selected from the group consisting of phosphoric acid, potassium dihydrogen phosphate, phosphorous acid and calcium phosphate.

Based on extensive experimental studies, the inventor found that the modification of the support with phosphorus could significantly improve the hydrogenation activity and stability of the catalyst, in particular hydrothermal stability. Particularly, the simultaneous introduction of an active auxiliary component (active auxiliary metal) in the catalyst had remarkable technical effects in respect of improving the conversion of α,α-dimethylbenzyl alcohol and the selectivity of isopropylbenzene.

In a preferred embodiment, if the support substrate is not silica, the modifying auxiliary component may further include silica.

In the catalyst of the present invention, the modification with silica (especially for modifying the support substrate of alumina) can improve the activity and stability of the catalyst. Preferably, alumina is used as the support substrate herein.

In a preferred embodiment (wherein the support substrate is not silica), the content of silica in the catalyst is >0-60 wt %, preferably >0-40 wt %, for example, >0-20 wt %, wherein the content of silica is based on the content of its molecules.

Here, the pore size of the catalyst increases after the modification with silicon, as improves the diffusion rate of the reactants and the product, thereby improving the conversion and the selectivity. In addition, it is also found that a silicon-containing catalyst has a better dehydration activity which is conducive to accelerate the rate of hydrogenolysis reaction.

In a preferred embodiment (wherein the support substrate is not silica), after the modification with silicon, the molar ratio of the silicon to phosphorus based on the element is ≤20, preferably ≤10, more preferably ≤4, but not 0, wherein the content of the modifying auxiliary component of phosphorus and/or oxides thereof in the catalyst is 0.2-20 wt %, preferably 1-15 wt %, more preferably 1-7 wt %, wherein the content of phosphorus and/or oxides thereof is based on the content of element phosphorus therein, and the silica content in the catalyst is >0-60 wt %, preferably >0-40 wt %, for example, >0-20 wt %.

In this way, the high-temperature hydrothermal stability of the catalyst can be significantly improved. For example, the change of the specific surface area and the average pore size of the catalyst after the high-temperature hydrothermal treatment is significantly reduced. For example, preferably, the change of the specific surface area is less than 30% and the change of the average pore size is less than 20%; more preferably, the change of the specific surface area of the catalyst is less than 10% and the change of the average pore size is less than 10%.

Here, the temperature of the high-temperature hydrothermal treatment is 100-300° C. and the period of the treatment is 20-300 hours.

The high-temperature hydrothermal stability is determined according to the following steps:

(a) Specific steps of high-temperature hydrothermal treatment of a catalyst: the catalyst is dispersed in excess water; then, the catalyst together with the water is placed in a crystallization kettle; after the crystallization kettle is sealed, it is placed in an oven of 200° C. for 240 hours.

(b) A method for determining the specific surface area and the pore size of the catalyst comprises the following specific analysis steps: the physical properties of the catalyst support and the catalyst (such as the specific surface area, pore size, pore volume and the like) are analyzed by nitrogen physical adsorption (ASAP 2020M, Micromeritics). Before analysis and tests, the sample is degassed in vacuum at 300° C. for 3 hours to remove the adsorbed impurities and moisture in the sample. After that, the nitrogen adsorption-desorption isotherm of the test sample is analyzed under a liquid nitrogen environment (−196° C.).

The specific surface area ($S_{BET}$) of the sample is calculated based on the nitrogen adsorption data under the relative pressure $P/P_0$ in the range of 0.05-0.20 according to BET equation (3-1):

$$\frac{P}{V(P_0 - P)} = \frac{1}{V_m C} + \frac{(C-1)P}{V_m C P_0} \quad (3-1)$$

wherein P is the pressure practically measured; P0 is the saturated vapor pressure at the adsorption temperature; V is the adsorption volume of nitrogen under pressure P; Vm is the volume of nitrogen required for monolayer saturated adsorption; C is the adsorption heat constant.

The pore size distribution ($D_p$) of the sample is calculated by BJH method (Barret-Joyner-Halensa) which is based on the phenomenon of capillary condensation. That is, the vapor pressure P and the radius of curvature of the liquid $r_k$ is in the following relationship:

$$\ln\left(\frac{P}{P_0}\right) = -\frac{2r \cdot V_m \cdot \cos\theta_k}{RT \cdot r_k} \quad (3-2)$$

wherein r is the surface tension of liquid nitrogen of $10^{-5}$ N/cm; $V_m$ is the molar volume of liquid nitrogen; $\theta_k$ is the contact angle between the meniscus and the solid hole wall; R is the ideal gas constant; T is the test temperature. Adsorption capacity V under different pressure P/P0 was obtained in the experiments. The relationship between V and $r_k$ is obtained by formula (3-2). Plotting of $r_k$ with $dV/dr_k$ results in the curve of the pore size distribution of the sample.

In a preferred embodiment, the catalyst further includes a co-catalyst; more preferably, the co-catalyst is a sulfur-containing compound which is preferably derived from a sulfur-containing organic matter.

Preferably, the support and the active component supported thereon are the catalyst main body on which the co-catalyst is supported.

In a further preferred embodiment, the content of the co-catalyst in the catalyst is >0-1 wt %, preferably >0-0.8 wt %, wherein the amount of the co-catalyst is based on the amount of effective elements therein, for example, the amount of element sulfur.

In the present invention, the source of the sulfur-containing compound is not particularly limited, preferably but not limited to at least one selected from the group of tert-nonyl polysulfides, tert-butyl polysulfides, thiophenes and dimethyl disulfides etc.

The sulfur-containing compound is preferentially adsorbed on the low coordination unsaturated active center on the catalyst surface, which causes the local poisoning phenomenon of an unstable active center on the catalyst. In this way, it can better inhibit the local overheating of the catalyst caused by a relatively high initial activity of the catalyst, and avoid the growth of metal grains and the excessive hydrogenation of isopropylbenzene to isopropylcyclohexane. Meanwhile, it can effectively control the generation of dimerized isopropyl benzene (2,3-dimethyl-2,3-diphenylbutane), significantly improving the operation stability of the catalyst while enhancing the selectivity of isopropylbenzene.

The metal palladium on the catalyst is free of a compressed double-bridge-bonded CO adsorption site. Preferably, there is no absorption peak in the range of 2000-1950 $cm^{-1}$ in the in situ infrared spectrogram of carbon monoxide adsorption of the catalyst.

In a preferred embodiment, the metal palladium on the catalyst contains a linear-bonded CO adsorption site, a mono-bridge-bonded CO adsorption site and a face-bonded CO adsorption site. In a further preferred embodiment, there are absorption peaks in the ranges of 2150-2050 $cm^{-1}$, 1950-1900 $cm^{-1}$ and 1900-1850 $cm^{-1}$ in the in situ infrared spectrogram of carbon monoxide adsorption of the catalyst.

In general, a metal palladium catalyst has four CO adsorption sites of special characteristics which respectively correspond to the noticeable absorption peaks in ranges of 2150-2050 $cm^{-1}$, 2000-1950 $cm^{-1}$, 1950-1900 $cm^{-1}$ and 1900-1850 $cm^{-1}$ in the CO-FTIR spectrogram. Said absorption peaks respectively belong to the linear-bonded CO adsorption site, compressed double-bridge-bonded CO adsorption site, mono-bridge-bonded CO adsorption site and face-bonded CO adsorption site of CO on the Pd surface.

The infrared spectrogram of CO adsorbed on the catalyst surface is determined as follows:

CO Fourier Transform Infrared spectrogram (CO-FTIR): FT-IR test of CO adsorption is carried out on an infrared spectrometer of THERMO NICOLET 4700 NEXUS with a resolution of 4 $cm^{-1}$. A sample is subjected to a pre-treatment of reduction in a Harrick in situ pool. The background spectrogram is first scanned at the test temperature before introducing CO gas for adsorption. Upon adsorption equilibrium, the sample is purged with nitrogen until no gas-phase infrared absorption peak of CO can be detected. The infrared spectrogram at the determination temperature is collected and the background spectrogram at the corresponding temperature is subtracted to obtain the infrared spectrogram of CO adsorbed on the catalyst surface.

The second object of the present invention is to provide a method for producing the catalyst according to the first object of the present invention, comprising the following steps:

Step 1: an aqueous solution of a phosphorus-containing compound is mixed with a support substrate, dried and calcined to obtain a phosphorus-containing support;

Step 2: the support is added to a solution of a palladium-containing compound, dried and calcined to obtain a catalyst precursor in an oxidized state;

Step 3: the catalyst precursor in an oxidized state is subjected to a reduction treatment to obtain a catalyst.

In a preferred embodiment, step 1' is optionally performed after step 1 and before step 2:

Step 1': the phosphorus-containing support is mixed with an aqueous solution of silica gel, dried and calcined to obtain a support containing phosphorus and silicon.

In a preferred embodiment, in step 1, step 2 and step 1', the drying is carried out by drying at 60-200° C. for 4-36 hours, preferably at 150° C. for 6 hours, or preferably at 110° C. for 8 hours.

In a preferred embodiment, in step 1, step 2 and step 1', the calcining temperature is 400-700° C., preferably 400-500° C.

In the present invention, the phosphorus-containing compound in step 1 is not particularly limited, preferably but not limited to at least one selected from the group consisting of phosphoric acid, potassium dihydrogen phosphate, phosphorous acid, calcium phosphate and ammonium hydrogen phosphate, etc.

In a preferred embodiment, the solution of a palladium-containing compound in step 2 further comprises a compound containing an active auxiliary metal.

In the present invention, unless otherwise specified, the support substrate is not particularly limited, preferably at least one selected from the group consisting of alumina, silica and activated carbon, more preferably alumina; the palladium-containing compound is not particularly limited, preferably but not limited to at least one selected from the group consisting of palladium chloride, palladium nitrate and chloropalladic acid; the compound containing an active auxiliary metal is not particularly limited, for example but not limited to at least one selected from the group consisting of active auxiliary metal chlorides, compounds of active auxiliary metal nitrates and compounds of active auxiliary metal acetates and the like; preferably, the active auxiliary metal is at least one selected from the group consisting of metal copper, metal zinc, metal cobalt, metal tin, metal nickel and metal silver, for example, metal copper.

In a preferred embodiment, in step 3, the reduction treatment is carried out with hydrogen. In a further preferred embodiment, the reduction temperature in step 3 is 40-300° C., preferably 200-300° C., more preferably 250° C.; the volume space velocity of hydrogen is 50-500 $h^{-1}$, preferably 80-150 $h^{-1}$, more preferably 100 $h^{-1}$.

In a preferred embodiment, the method further comprises step 4:

Step 4: the catalyst according to step 3 is added to a co-catalyst-containing solution and dried to obtain a further catalyst.

In a further preferred embodiment, the co-catalyst is a sulfur-containing compound; more preferably, the sulfur-containing compound is derived from a sulfur-containing organic matter; further preferably, the sulfur-containing organic matter is at least one selected from the group of tert-nonyl polysulfides, tert-butyl polysulfides, thiophenes and dimethyl disulfides.

In the production method according to the present invention, the amounts of the palladium-containing compound and the phosphorus-containing compound based on 1 L of the support substrate are as follows:

the amount of the palladium-containing compound is preferably 0.06 g/L-30 g/L, more preferably 0.5 g/L-10 g/L, based on the amount of element palladium therein, and;

the amount of the phosphorus-containing compound is preferably 2 g/L-100 g/L, more preferably 5 g/L-80 g/L, based on the amount of element phosphorus therein.

If present, the amounts of the compound containing an active auxiliary metal, the silica gel and/or the sulfur-containing organic matter are based on 1 L of the support substrate as follows:

the amount of the compound containing an active auxiliary metal is preferably 0.0006 g/L-1.2 g/L, more preferably 0.01 g/L-1.0 g/L, based on the amount of the element of the active auxiliary metal therein;

the amount of silica gel is 6-300 g/L, more preferably 20-200 g/L, wherein the amount of silica gel is based on the amount of silica therein;

the amount of the co-catalyst, e.g., a sulfur-containing compound, is 0.0001 g/L-3 g/L, preferably 0.01 g/L-1 g/L, more preferably 0.05 g/L-0.2 g/L, wherein the amount of the sulfur-containing compound is based on the amount of effective elements therein, such as element sulfur.

In the method for producing a catalyst of the present invention, all solutions are those formed by fully dissolving solutes in their good solvents, preferably aqueous solutions.

The third object of the present invention is to provide the use of the catalyst according to the first object of the present invention or the catalyst obtained by the method according to the second object of the present invention in the production of isopropylbenzene.

The fourth object of the present invention is to provide a method for producing isopropylbenzene, in particular, a method for producing isopropylbenzene from α,α-dimethylbenzyl alcohol, preferably carried out with the catalyst according to the first object of the present invention or the catalyst obtained by the method according to the second object of the present invention.

In a preferred embodiment, the production method comprises: bring the raw material in contact with hydrogen to react in the presence of the catalyst to obtain isopropylbenzene. In a further preferred embodiment, the raw material comprise a hydrocarbon material comprising α,α-dimethylbenzyl alcohol. In a further preferred embodiment, the hydrocarbon material comprising α,α-dimethylbenzyl alcohol comprises an inert solvent (preferably isopropylbenzene) and α,α-dimethylbenzyl alcohol. For example, the hydrocarbon material is the column bottom liquid after propylene oxide is separated in the production of propylene oxide in the isopropylbenzene hydroperoxide process, and/or the material obtained from the reduction of isopropylbenzene hydroperoxide. Here, the inert solvent must be substantively inactive to the reactants and the resultants, for example, long-chain alkanes (octane, dodecane) and aromatic monocyclic aromatic hydrocarbons (benzene, toluene, ethylbenzene, n-propyl benzene, n-butyl benzene, isopropylbenzene), etc. Specifically, the inert solvent is a hydrocarbon substantively inactive to the reactants and the resultants. Moreover, the solvent can be an organic solvent having a good compatibility with dimethylbenzyl alcohol, but preferably isopropylbenzene which does not affect the subsequent reaction.

In a preferred embodiment, the raw material comprises 1-100% of α,α-dimethylbenzyl alcohol and 0-99% of an inert solvent (preferably isopropylbenzene). In a further preferred embodiment, the raw material comprises 50-75% of α,α-dimethylbenzyl alcohol and 25-50% of an inert solvent (preferably isopropylbenzene).

In the present invention, the specific content of each component in the raw material is not particularly limited. As a non-restrictive example, the raw material comprise about 55 wt % of a hydrocarbon material of α,α-dimethylbenzyl alcohol, about 43 wt % of isopropylbenzene and other hydrocarbons in content of about 2 wt %, based on the weight percentage. The other hydrocarbons may include n-propyl benzene, methylstyrene, acetophenone and 2,3-dimethyl-2,3-diphenylbutane.

In a preferred embodiment, the pressure is 0.1-4.0 MPa, the temperature is 130-220° C., the liquid hourly space velocity is 1-20 $h^{-1}$, and the molar ratio of hydrogen to α,α-dimethylbenzyl alcohol is >4 in the production method. In a further preferred embodiment, the pressure is 0.5-3.0 MPa, the temperature is 150-200° C., the liquid hourly space velocity is 4-15 $h^{-1}$, and the molar ratio of hydrogen to α,α-dimethylbenzyl alcohol is >5.

In a preferred embodiment, the production method employs the liquid phase thermal cycle process. Preferably, the cycle ratio is 1-10, preferably 4-8. The "liquid phase thermal cycle process" herein refers to a direct circulation of the liquid phase thermal material at the outlet of a catalyst bed to the catalyst bed without cooling and water separation.

In a preferred embodiment, the production method of the present invention comprises obtaining the isopropylbenzene from raw material of a hydrocarbon material comprising α,α-dimethylbenzyl alcohol and hydrogen through a first catalyst bed and a second catalyst bed in series, preferably by the liquid phase thermal cycle process;
wherein,
the catalyst loading of the first catalyst bed is greater than or equal to that of the second catalyst bed;
the inlet temperature of the first catalyst bed is not higher than the inlet temperature of the second catalyst bed;
the liquid phase thermal cycle ratio of the first catalyst bed is preferably 1-10;
the liquid phase thermal cycle ratio of the second catalyst bed is preferably 0-2.

In a preferred embodiment, the ratio by volume of the catalyst loading of the first catalyst bed to the catalyst loading of the second catalyst bed is (1-6):1, preferably (2-4):1.

In the first catalyst bed, the ratio by volume of hydrogen to the liquid phase is preferably 300-1000, more preferably 400-800, and/or; in the second catalyst bed, the ratio by volume of hydrogen to the liquid phase is preferably 100-800, more preferably 200-400.

In a preferred embodiment, the first catalyst bed has a reaction temperature of 130-190° C., a reaction pressure of 0.1-5 MPa, and a liquid hourly space velocity of 1.0-20 h$^{-1}$. In a further preferred embodiment, the first catalyst bed has a reaction temperature of 150-170° C., a reaction pressure of 0.5-3.0 MPa, a liquid phase volume space velocity of 1-5$^{-1}$, and a cycle ratio of 2-8.

Here, the liquid phase is a fresh oil which refers to a raw material feed that has not undergone a dilution by the liquid phase thermal cycle process. In a preferred embodiment, the second catalyst bed has a reaction temperature of 150-230° C., a reaction pressure of 0.1-5 MPa, and a liquid phase volume space velocity of 2.0-10 h$^{-1}$. In a further preferred embodiment, the second catalyst bed has a reaction temperature of 160-190° C., a reaction pressure of 0.5-3 MPa, and a liquid hourly space velocity of 4-8 h$^{-1}$.

Preferably, the catalyst of the first catalyst bed comprises metal Pd and/or oxides, and a support.

Preferably, the catalyst of the second catalyst bed comprises metal Pd and/or oxides, a metal auxiliary and/or oxides thereof, and a support; preferably, the metal auxiliary is at least one selected from the group consisting of Fe, Co, Ni, Ca, Mg and Cu, more preferably at least one selected from the group consisting of Cu, Ni and Mg.

Preferably, the catalyst of the first catalyst bed and/or the catalyst of the second catalyst bed are the catalysts for producing isopropylbenzene as provided in the first object of the present invention.

In the present invention, the loading of the first catalyst bed is set to be greater than or equal to, preferably significantly higher than the loading of the second catalyst bed, so that the raw material can react in the first catalyst bed as much as possible. If there is unreacted raw material, it enters the second catalyst bed for a reaction at a slightly higher temperature.

Specifically, when the concentration of reactants in the raw material is high, the heat release in the reaction process is high, so the first bed adopts the mode of the liquid phase thermal cycle, having a high total volume space velocity and a function of carrying heat to prevent an overheating of the bed and a formation of local hot spots, as is conducive to the selectivity and stability of the catalyst. Whereas, the second bed which employs a higher temperature realizes a high conversion of a small amount of remained reactants. In this way, the impurity content in the product is significantly reduced.

In a preferred embodiment, the conversion of α,α-dimethylbenzyl alcohol is greater than 99.5% and the selectivity of isopropylbenzene is greater than 99.8% in the method for producing isopropylbenzene from α,α-dimethylbenzyl alcohol.

The conversion and the selectivity are calculated according to the following formula:

$$\alpha,\alpha\text{-dimethylbenzyl alcohol conversion (\%)}=[(W^o_1-W^t_1)/W^o_1]\times 100\%;$$

$$\text{Isopropylbenzene selectivity (\%)}=[((W^t_2-W^o_2)/M_2)/((W^o_1-W^t_1)/M_1)]\times 100\%;$$

wherein, $w^o_1$ denotes the mass of α,α-dimethylbenzyl alcohol in the raw material; $w^t_1$ denotes the mass of α,α-dimethylbenzyl alcohol in the product; $w^o_2$ notes the mass of isopropylbenzene in the raw material; $w^t_2$ denotes the mass of isopropylbenzene in the product; $M_1$ denotes the molecular weight of α,α-dimethylbenzyl alcohol; $M_2$ denotes the molecular weight of isopropylbenzene.

The method for producing isopropylbenzene from α,α-dimethylbenzyl alcohol according to the present invention provides a suitable dehydrating acid site and a hydrogenating metal active site, better inhibits the local overheating of the catalyst caused by a relatively high initial activity of the catalyst, avoids the growth of metal grains and the excessive hydrogenation of isopropylbenzene to isopropylcyclohexane in the catalytic process of producing isopropylbenzene by dehydration and hydrogenation of α,α-dimethylbenzyl alcohol in the presence of a supported palladium active component. Meanwhile, it effectively controls the generation of dimerized isopropyl benzene and significantly improves the operation stability of the catalyst while enhancing the selectivity of isopropylbenzene.

The present invention further provides the use of the said production method in the production of propylene oxide, for example by:
Step 1: obtaining isopropylbenzene hydroperoxide by oxidation of isopropylbenzene;
Step 2: obtaining propylene oxide and α,α-dimethylbenzyl alcohol from the reaction of isopropylbenzene hydroperoxide and propylene;
Step 3: obtaining a hydrocarbon material comprising α,α-dimethylbenzyl alcohol by means of a separation of propylene oxide by rectification;
Step 4: subjecting the hydrocarbon material comprising α,α-dimethylbenzyl alcohol to a treatment with the catalyst and the method in the present invention to obtain isopropylbenzene which is recycled to step 1 for reuse.

The endpoints and any values of the ranges disclosed in the present invention are not limited to the precise ranges or values. These ranges or values should be interpreted as including the values close to these ranges or these values. In regard of number ranges, between the endpoints of each range, between the endpoints of each range and the individual values, and between the individual values, they can be combined with each other to obtain one or more new number ranges. It should be regarded that these number ranges are specifically disclosed in the present invention. Various technical solutions in the context can be combined with each other in principle to obtain new technical solutions, which should also be regarded as being specifically disclosed in the present invention.

The present invention at least has the following advantageous effects compared with the prior art:
(1) the addition of a modifying auxiliary component P in the support of the catalyst according to the present invention can significantly improve and increase the hydrogenation activity and the stability of the catalyst. In particular, the addition of the modifying auxiliary components P and SiO$_2$ in the support can significantly improve the hydrothermal stability of the catalyst when the molar ratio of silicon to phosphorus is of a certain value.

(2) the simultaneous introduction of the active auxiliary component in the catalyst can significantly improve the conversion of α,α-dimethylbenzyl alcohol and the selectivity of isopropylbenzene.

(3) the introduction of a co-catalyst in the catalyst avoids the excessive hydrogenation of isopropylbenzene to isopropylcyclohexane. Meanwhile, it can effectively control the generation of dimerized isopropyl benzene (2,3-dimethyl-2,3-diphenylbutane), and significantly improve the operation stability of the catalyst while enhancing the selectivity of isopropylbenzene.

(4) in the method for producing isopropylbenzene by the liquid phase thermal cycle provided in the present invention, the utilization of the reaction heat is more reasonable, as can significantly reduce the energy consumption and costs of the device and produce isopropylbenzene efficiently.

(5) the method for producing isopropylbenzene according to the present invention provides a suitable dehydrating acid site and hydrogenating metal active site, better inhibits the excessive hydrogenation of isopropylbenzene to isopropylcyclohexane due to the local overheating of the catalyst caused by a relatively high initial activity of the catalyst in the catalytic process of producing isopropylbenzene by dehydration and hydrogenation of α,α-dimethylbenzyl alcohol in the presence of a supported palladium active catalyst. Meanwhile, it effectively controls the generation of dimerized isopropyl benzene and significantly improves the operation stability of the catalyst while enhancing the selectivity of isopropylbenzene.

In conclusion, the present invention produces a hydrogenolysis catalyst having good properties, realizes the coupling of two reactions of dehydration and hydrogenation and utilizes energy more reasonably by using the liquid phase thermal cycle process by means of producing a support having a good hydrothermal stability and an excellent dehydration property and supporting hydrogenating metals using the support. Meanwhile, the present invention prevents the decrease in the performance of the catalyst caused by the local overheating of the catalyst bed and realizes a low-cost and highly-efficient production of isopropylbenzene.

BRIEF DESCRIPTION OF DRAWINGS

FIG. 1 shows the CO-FTIR analysis results of Examples 3 and 6.

MODE FOR CARRYING OUT THE INVENTION

The present invention is described in detail in combination with specific examples as below. It is necessary to point out that the following examples which are only used for further illustration of the present invention cannot be interpreted as a limitation on the protection scope of the present invention. Non-essential improvements and adjustments made by those skilled in the art to the present invention according to the contents of the present invention are still in the protection scope of the invention.

Table 1 shows the components of the raw material used in the examples and the comparative examples.

TABLE 1

Components of the used raw material

| Components of raw material | Components by weight w % |
|---|---|
| isopropylbenzene | 43.25 |
| n-propyl benzene | 0.08 |
| methyl styrene | 0.12 |
| acetophenone | 1.02 |
| a,a-dimethylbenzyl alcohol | 55.26 |
| dimerized isopropylbenzene (2,3-dimethyl-2,3-diphenylbutane) | 0.27 |

Analysis of the content of each component in the catalyst: the specific element composition in the catalyst is determined by X-ray fluorescence analysis method. Different elements have characteristic X-ray spectrogram with different wavelengths, and the fluorescence intensity of each spectral line has a certain relationship with the concentration of the element. Qualitative and quantitative analysis can be performed by determining the wavelength and intensity of the characteristic X-ray spectral lines of the elements to be tested.

I. Production and Evaluation of Catalysts

Example 1

1. Catalyst Production

1 L of alumina was mixed with 600 g of aqueous solution of phosphoric acid containing 8.0 g of P, dried at 110° C. for 8 hours and calcined at 400° C. for 4 hours to produce a catalyst support.

1 L of the above support was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 250° C. to produce a palladium-based catalyst. The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:

Reaction temperature: 150° C.

Reaction pressure: 2.0 MPa

Volume space velocity of raw material fresh oil: 1.6 h$^{-1}$

Liquid phase thermal cycle ratio: 4

Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 2

1. Catalyst Production

1 L of alumina was mixed with 600 g of aqueous solution of phosphoric acid containing 8.0 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

Example 3

1. Catalyst Production

1 L of alumina was mixed with 600 g of aqueous solution of phosphoric acid containing 27 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

The major components and properties of the catalyst are shown in Table 2 and Table 3. The CO-FTIR analysis results are shown in FIG. 1.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 4

1. Catalyst Production

1 L of alumina was mixed with 600 g of aqueous solution of phosphoric acid containing 35 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 5

1. Catalyst Production

1 L of alumina was mixed with 600 g of aqueous solution of phosphoric acid containing 5.0 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 6

1. Catalyst Production

1 L of alumina was mixed with 600 g of aqueous solution of phosphoric acid containing 27 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst precursor II.

1 L of the above palladium-based catalyst precursor II was impregnated with 550 g of cyclohexane solution of tert-nonyl polysulfide containing 0.1 g of sulphur and dried at 110° C. to obtain a palladium-based catalyst.

The major components and properties of the catalyst are shown in Table 2 and Table 3. The CO-FTIR analysis results are shown in FIG. 1.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 7

1. Catalyst Production

1 L of alumina was mixed with 600 g of aqueous solution of phosphoric acid containing 35 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst precursor II.

1 L of the above palladium-based catalyst precursor II was impregnated with 550 g of cyclohexane solution of tert-nonyl polysulfide containing 0.1 g of sulphur and dried at 110° C. to obtain a palladium-based catalyst. The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 1000 hour evaluation are shown in Table 5.

Example 8

The process in Example 2 was repeated, except that the aqueous solution of chloropalladic acid-nickel nitrate contained 10.0 g of palladium and 1.2 g of nickel. The major components of the catalyst are shown in Table 2.

The catalyst evaluation in Example 2 was repeated. Likewise, the conversion of α,α-dimethylbenzyl alcohol and the selectivity of isopropylbenzene were both relatively high.

Example 9

The process in Example 2 was repeated, except that the aqueous solution of chloropalladic acid-cobalt nitrate contained 0.5 g of palladium and 0.0006 g of cobalt. The major components of the catalyst are shown in Table 2.

The catalyst evaluation in Example 2 was repeated. Likewise, the conversion of α,α-dimethylbenzyl alcohol and the selectivity of isopropylbenzene were both relatively high.

Examples 10-13

The process in Example 7 was repeated, except that di-tertnonyl polysulfides containing 0.01 g, 0.05 g, 0.2 g and 1 g of sulphur were respectively employed. The major components of the catalyst are shown in Table 2.

The catalyst evaluation in Example 7 was repeated. Likewise, the conversion of α,α-dimethylbenzyl alcohol and the selectivity of isopropylbenzene were both relatively high.

Example 14

The process in Example 6 was repeated, except that in the catalyst production:

1 L of alumina was mixed with 600 g of aqueous solution of phosphoric acid containing 27 g of P, dried at 110° C. for 8 hours and calcined at 400° C. for 4 hours to produce a catalyst support containing P.

1 L of the above catalyst support containing P was mixed with 600 g of aqueous solution of silica gel having a mass concentration of 5% of $SiO_2$, dried and calcined at 500° C. to obtain a support containing P/Si.

1 L of the above support containing P/Si was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst precursor II.

1 L of the above palladium-based catalyst precursor II was impregnated with 550 g of cyclohexane solution of tert-nonyl polysulfide containing 0.1 g of sulphur to obtain a palladium-based catalyst. The major components of the catalyst are shown in Table 2.

The catalyst evaluation in Example 6 was repeated. Likewise, the conversion of α,α-dimethylbenzyl alcohol and the selectivity of isopropylbenzene were both relatively high.

The physical properties of the catalyst after high-temperature hydrothermal treatment are shown in Table 4.

Example 15

The process in Example 6 was repeated, except that in the catalyst production:

1 L of alumina was mixed with 600 g of aqueous solution of phosphoric acid containing 27 g of P, dried at 110° C. for 8 hours and calcined at 400° C. for 4 hours to produce a catalyst support containing P.

1 L of the above catalyst support containing P was mixed with 600 g of aqueous solution of silica gel having a mass concentration of 10% of $SiO_2$, dried and calcined at 500° C. to obtain a support containing P/Si.

1 L of the above support containing P/Si was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst precursor II.

1 L of the above palladium-based catalyst precursor II was impregnated with 550 g of cyclohexane solution of tert-nonyl polysulfide containing 0.1 g of sulphur to obtain a palladium-based catalyst. The major components of the catalyst are shown in Table 2.

The support employed in the catalyst obtained in Example 15 contained not only P but also silicon. In the production of isopropylbenzene by hydrogenation of α,α-dimethylbenzyl alcohol using the catalyst, the conversion of α,α-dimethylbenzyl alcohol and the selectivity of isopropylbenzene were both higher than those in Example 6.

The physical properties of the catalyst after high-temperature hydrothermal treatment are shown in Table 4.

Example 16

The process in Example 6 was repeated, except that in the catalyst production:

1 L of alumina was mixed with 600 g of aqueous solution of phosphoric acid containing 27 g of P, dried at 110° C. for 8 hours and calcined at 400° C. for 4 hours to produce a catalyst support containing P.

1 L of the above catalyst support containing P was mixed with 600 g of aqueous solution of silica gel having a mass concentration of 20% of $SiO_2$, dried and calcined at 500° C. to obtain a support containing P/Si.

1 L of the above support containing P/Si was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst precursor II.

1 L of the above palladium-based catalyst precursor II was impregnated with 550 g of cyclohexane solution of tert-nonyl polysulfide containing 0.1 g of sulphur to obtain a palladium-based catalyst. The major components of the catalyst are shown in Table 2.

The physical properties of the catalyst after high-temperature hydrothermal treatment are shown in Table 4.

Example 17

The process in Example 6 was repeated, except that in the catalyst production:

1 L of alumina was mixed with 600 g of aqueous solution of phosphoric acid containing 27 g of P, dried at 110° C. for 8 hours and calcined at 400° C. for 4 hours to produce a catalyst support containing P.

1 L of the above catalyst support containing P was mixed with 600 g of aqueous solution of silica gel having a mass concentration of 30% of $SiO_2$, dried and calcined at 500° C. to obtain a support containing P/Si.

1 L of the above support containing P/Si was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst precursor II.

1 L of the above palladium-based catalyst precursor II was impregnated with 550 g of cyclohexane solution of tert-nonyl polysulfide containing 0.1 g of sulphur to obtain a palladium-based catalyst. The major components of the catalyst are shown in Table 2.

The physical properties of the catalyst after high-temperature hydrothermal treatment are shown in Table 4.

Analysis of Examples 14-17: the supports employed in the catalysts obtained in Examples 14-17 contained not only P, but also silicon and sulfur. When the above were used in the production of isopropylbenzene by hydrogenation of α,α-dimethylbenzyl alcohol, both the conversion of α,α-dimethylbenzyl alcohol and the selectivity of isopropylbenzene were higher than those in Example 6.

Example 18

The process of Example 14 was repeated, except that in the catalyst evaluation:

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner. The material first passed through the first catalyst bed, and then through the second catalyst bed. The catalyst loading volume ratio of the two catalyst beds was 4:1. The operating conditions of the two reactors were as follows:

The First Catalyst Bed:
  Inlet temperature: 150° C.
  Reaction pressure: 2.0 MPa
  Volume space velocity of raw material fresh oil: 2.0 $h^{-1}$
  Liquid phase thermal cycle ratio: 4
  Hydrogen/α,α-dimethylbenzyl alcohol molar ratio: 8

The Second Catalyst Bed:
  Inlet temperature: 160° C.
  Reaction pressure: 2.0 MPa
  Liquid phase thermal cycle ratio: 0

The average results of 200 hour evaluation are shown in Table 5.

Example 19

1. Catalyst Production

1 L of alumina was mixed with 600 g of aqueous solution of phosphoric acid containing 8.0 g of P, dried at 110° C. for 8 hours and calcined at 400° C. for 4 hours to produce a catalyst support.

1 L of the above catalyst support containing P was mixed with 600 g of aqueous solution of silica gel having a mass concentration of 10% of $SiO_2$, dried and calcined at 500° C. to obtain a support containing P/Si.

1 L of the above support was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state. The above palladium-based catalyst precursor I in an oxidized state was reduced with hydrogen having a volume space velocity of 100 $hour^{-1}$ for 4 hours at a reduction temperature of 250° C. to produce a palladium-based catalyst. The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
  Reaction temperature: 150° C.
  Reaction pressure: 2.0 MPa
  Volume space velocity of raw material fresh oil: 1.6 $h^{-1}$
  Liquid phase thermal cycle ratio: 4
  Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 20

1. Catalyst Production

1 L of alumina was mixed with 600 g of aqueous solution of phosphoric acid containing 8.0 g of P, dried at 110° C. for 8 hours and calcined at 400° C. for 4 hours to produce a catalyst support.

1 L of the above support was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 $hour^{-1}$ for 4 hours at a reduction temperature of 250° C. to produce a palladium-based catalyst.

1 L of the above palladium-based catalyst precursor was impregnated with 550 g of cyclohexane solution of tert-nonyl polysulfide containing 0.1 g of sulphur to obtain a palladium-based catalyst. The major components and properties of the catalyst are shown in Table 2.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
  Reaction temperature: 150° C.
  Reaction pressure: 2.0 MPa
  Volume space velocity of raw material fresh oil: 1.6 $h^{-1}$
  Liquid phase thermal cycle ratio: 4
  Hydrogen/α,α-dimethylbenzyl alcohol molar ratio: 8

The average results of 200 hour evaluation are shown in Table 5.

Example 21

1. Catalyst Production

1 L of alumina was mixed with 600 g of aqueous solution of phosphoric acid containing 8.0 g of P, dried at 110° C. for 8 hours and calcined at 400° C. for 4 hours to produce a catalyst support.

1 L of the above catalyst support containing P was mixed with 600 g of aqueous solution of silica gel having a mass concentration of 10% of $SiO_2$, dried and calcined at 500° C. to obtain a support containing P/Si.

1 L of the above support was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 $hour^{-1}$ for 4 hours at a reduction temperature of 250° C. to produce a palladium-based catalyst.

1 L of the above palladium-based catalyst precursor was impregnated with 550 g of cyclohexane solution of tert-nonyl polysulfide containing 0.1 g of sulphur to obtain a palladium-based catalyst. The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
  Reaction temperature: 150° C.
  Reaction pressure: 2.0 MPa
  Volume space velocity of raw material fresh oil: 1.6 $h^{-1}$
  Liquid phase thermal cycle ratio: 4
  Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Example 22

1. Catalyst Production

1 L of alumina was mixed with 600 g of aqueous solution of phosphoric acid containing 8.0 g of P, dried at 110° C. for 8 hours and calcined at 400° C. for 4 hours to produce a catalyst support.

1 L of the above catalyst support containing P was mixed with 600 g of aqueous solution of silica gel having a mass concentration of 10% of $SiO_2$, dried and calcined at 500° C. to obtain a support containing P/Si.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 $hour^{-1}$ for 4 hours at a reduction temperature of 250° C. to produce a palladium-based catalyst. The major components of the catalyst are shown in Table 2.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 $h^{-1}$
Liquid phase thermal cycle ratio: 4
Hydrogen/α,α-dimethylbenzyl alcohol molar ratio: 8

The average results of 200 hour evaluation are shown in Table 5.

Example 23

1. Catalyst Production

1 L of alumina was mixed with 600 g of aqueous solution of phosphoric acid containing 4.0 g of P, dried at 110° C. for 8 hours and calcined at 400° C. for 4 hours to produce a catalyst support.

1 L of the above catalyst support containing P was mixed with 600 g of aqueous solution of silica gel having a mass concentration of 10% of $SiO_2$, dried and calcined at 500° C. to obtain a support containing P/Si.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 $hour^{-1}$ for 4 hours at a reduction temperature of 250° C. to produce a palladium-based catalyst. The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 $h^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Comparative Example 1

1. Catalyst Production

1 L of alumina was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state. The above palladium-based catalyst precursor I in an oxidized state was reduced with hydrogen having a volume space velocity of 100 $hour^{-1}$ for 4 hours at a reduction temperature of 250° C. to produce a palladium-based catalyst.

The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 $h^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Comparative Example 2

1. Catalyst Production

1 L of alumina was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state. The above palladium-based catalyst precursor I in an oxidized state was reduced with hydrogen having a volume space velocity of 100 $hour^{-1}$ for 4 hours at a reduction temperature of 250° C. to produce a palladium-based catalyst.

The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

Comparative Example 3

1. Catalyst Production

1 L of support alumina was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

1 L of the above palladium-based catalyst was impregnated with 550 g of cyclohexane solution of tert-nonyl polysulfide containing 0.1 g of sulphur to obtain a palladium-based catalyst. The major components of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Comparative Example 4

1. Catalyst Production

1 L of support alumina was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

1 L of the above palladium-based catalyst was impregnated with 550 g of cyclohexane solution of tert-nonyl polysulfide containing 0.1 g of sulphur to obtain a palladium-based catalyst. The major components of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

Comparative Example 5

1. Catalyst Production

1 L of support alumina was mixed with 600 g of aqueous solution of silica gel having a mass concentration of 10% of SiO$_2$, dried and calcined at 500° C. to obtain a support containing Si.

1 L of the above support was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst. The major components and properties of the catalyst are shown in Table 2.

The major components and properties of the catalyst are shown in Table 2 and Table 3.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

The physical properties of the catalyst after high-temperature hydrothermal treatment are shown in Table 4.

Comparative Example 6

1. Catalyst Production

1 L of support alumina was mixed with 600 g of aqueous solution of silica gel having a mass concentration of 10% of SiO$_2$, dried and calcined at 500° C. to obtain a support containing Si.

1 L of the above support was mixed with 2000 g of aqueous solution of chloropalladic acid containing 3.0 g of palladium, dried at 110° C. for 8 hours and calcined at 500° C. for 4 hours to produce a palladium-based catalyst precursor I in an oxidized state.

The above palladium-based catalyst precursor I in an oxidized state was reduced with hydrogen having a volume space velocity of 100 hour$^{-1}$ for 4 hours at a reduction temperature of 250° C. to produce a palladium-based catalyst.

1 L of the above palladium-based catalyst was impregnated with 550 g of cyclohexane solution of tert-nonyl polysulfide containing 0.1 g of sulphur to obtain a palladium-based catalyst. The major components of the catalyst are shown in Table 2.

The major components and properties of the catalyst are shown in Table 2.

2. Catalyst Evaluation

Hydrogenation operation was carried out in a fixed bed reactor which was filled with the catalyst produced as the above. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 200 hour evaluation are shown in Table 5.

TABLE 2

Major components of the catalysts

| Item | Al$_2$O$_3$ wt % | Pd wt % | M wt % | P wt % | S wt % | SiO$_2$ wt % |
|---|---|---|---|---|---|---|
| Example 1 | 95.24 | 0.458 | 0 | 1.39 | 0 | 0 |
| Example 2 | 95.24 | 0.458 | CuO-0.19 | 1.41 | 0 | 0 |
| Example 3 | 87.55 | 0.467 | CuO-0.18 | 4.6 | 0 | 0 |
| Example 4 | 84.45 | 0.466 | CuO-0.19 | 6.12 | 0 | 0 |
| Example 5 | 97.11 | 0.482 | CuO-0.19 | 0.89 | 0 | 0 |
| Example 6 | 87.47 | 0.457 | CuO-0.18 | 4.7 | 0.020 | 0 |
| Example 7 | 84.36 | 0.463 | CuO-0.19 | 6.27 | 0.021 | 0 |
| Example 8 | 94.32 | 1.527 | NiO-0.26 | 1.41 | 0 | 0 |
| Example 9 | 95.24 | 0.078 | CoO-0.00014 | 1.39 | 0 | 0 |
| Example 10 | 84.22 | 0.456 | CuO-0.226 | 6.28 | 0.0019 | 0 |
| Example 11 | 83.61 | 0.462 | CuO-0.225 | 6.31 | 0.010 | 0 |
| Example 12 | 83.58 | 0.459 | CuO-0.227 | 6.29 | 0.036 | 0 |
| Example 13 | 82.90 | 0.467 | CuO-0.223 | 6.33 | 0.200 | 0 |
| Example 14 | 81.86 | 0.452 | CuO-0.228 | 4.75 | 0.020 | 5.45 |
| Example 15 | 76.98 | 0.423 | CuO-0.226 | 4.67 | 0.021 | 10.62 |
| Example 16 | 64.25 | 0.478 | CuO-0.226 | 4.91 | 0.019 | 21.26 |
| Example 17 | 53.56 | 0.465 | CuO-0.224 | 4.76 | 0.020 | 33.05 |
| Example 19 | 85.32 | 0.458 | 0 | 1.39 | 0 | 10.62 |
| Example 20 | 95.86 | 0.458 | 0 | 1.39 | 0.021 | 0 |
| Example 21 | 85.25 | 0.458 | 0 | 1.39 | 0.021 | 10.62 |
| Example 22 | 85.11 | 0.458 | CuO-0.19 | 1.39 | 0 | 10.62 |
| Example 23 | 86.72 | 0.458 | CuO-0.19 | 0.72 | 0 | 10.62 |
| Comparative Example 1 | 99.21 | 0.471 | 0 | 0 | 0 | 0 |
| Comparative Example 2 | 99.17 | 0.467 | CuO-0.228 | 0 | 0 | 0 |
| Comparative Example 3 | 99.17 | 0.467 | CuO-0.19 | 0 | 0.021 | 0 |
| Comparative Example 4 | 99.36 | 0.467 | 0 | 0 | 0.021 | 0 |
| Comparative Example 5 | 88.66 | 0.467 | 0 | 0 | 0 | 10.62 |
| Comparative Example 6 | 88.61 | 0.467 | 0 | 0 | 0.021 | 10.62 |

TABLE 3

Physical properties of the obtained catalysts

| Item | Specific surface area m$^2$g | Average pore size nm | Pd dispersity % |
|---|---|---|---|
| Example 1 | 138 | 13.5 | 9.6 |
| Example 2 | 138 | 13.7 | 8.5 |
| Example 3 | 133 | 14.8 | 6.9 |
| Example 4 | 128 | 14.7 | 6.5 |
| Example 5 | 142 | 13.2 | 8.4 |
| Example 6 | 133 | 14.8 | 6.9 |
| Example 7 | 128 | 15.2 | 6.5 |
| Example 8 | 135 | 13.5 | 5.2 |
| Example 11 | 127 | 14.6 | 7.2 |
| Example 14 | 132 | 13.8 | 6.9 |
| Example 15 | 141 | 13.6 | 6.5 |
| Example 16 | 145 | 12.9 | 6.7 |
| Example 17 | 151 | 13.1 | 6.6 |
| Example 19 | 136 | 13.4 | 9.8 |
| Example 21 | 136 | 13.4 | 8.2 |
| Example 23 | 141 | 13.2 | 8.5 |
| Comparative Example 1 | 146 | 12.7 | 21.3 |
| Comparative Example 2 | 146 | 12.7 | 18.3 |
| Comparative Example 3 | 146 | 12.7 | 15.4 |
| Comparative Example 4 | 146 | 12.7 | 12.3 |
| Comparative Example 5 | 154 | 11.9 | 13.6 |

TABLE 4

Physical properties of the produced catalysts after high-temperature hydrothermal treatment

| Item | Specific surface area (m$^2$g) | Average pore size (nm) |
|---|---|---|
| Example 1 | 102 | 16.2 |
| Example 3 | 108 | 15.8 |
| Example 4 | 116 | 14.6 |
| Example 5 | 102 | 16.4 |
| Example 6 | 112 | 15.4 |
| Example 14 | 142 | 13.2 |
| Example 15 | 146 | 12.8 |
| Example 16 | 152 | 12.6 |
| Example 17 | 156 | 12.8 |
| Example 19 | 152 | 12.8 |
| Example 21 | 155 | 12.6 |
| Example 23 | 128 | 13.8 |
| Comparative Example 1 | 32 | 24.2 |
| Comparative Example 3 | 35 | 23.6 |
| Comparative Example 5 | 86 | 17.6 |

Table 4 proves that the physical properties of the catalysts of Examples 1, 3-6, 14-17, 19, 21 and 23 of the present invention after high-temperature hydrothermal treatment are excellent.

TABLE 5

Average results of 200 hour evaluation

| Item | Production quantity of isopropylcyclohexane ppm | Conversion of α,α-dimethylbenzyl alcohol % | Selectivity of isopropylbenzene % |
|---|---|---|---|
| Example 1 | 556 | 99.22 | 99.75 |
| Example 2 | 418 | 99.54 | 99.81 |
| Example 3 | 321 | 99.42 | 99.84 |
| Example 4 | 412 | 99.41 | 99.78 |
| Example 5 | 376 | 99.51 | 99.77 |
| Example 6 | 139 | 99.71 | 99.88 |
| Example 7 | 128 | 99.66 | 99.87 |
| Example 8 | 524 | 99.71 | 99.68 |
| Example 9 | 278 | 99.58 | 99.82 |
| Example 10 | 238 | 99.74 | 99.78 |

TABLE 5-continued

Average results of 200 hour evaluation

| Item | Production quantity of isopropylcyclohexane ppm | Conversion of α,α-dimethylbenzyl alcohol % | Selectivity of isopropylbenzene % |
|---|---|---|---|
| Example 11 | 185 | 99.81 | 99.81 |
| Example 12 | 89 | 99.65 | 99.92 |
| Example 13 | 45 | 99.52 | 99.88 |
| Example 14 | 16 | 99.75 | 99.90 |
| Example 15 | 14 | 99.75 | 99.87 |
| Example 16 | 12 | 99.70 | 99.86 |
| Example 17 | 15 | 99.70 | 99.86 |
| Example 18 | 6 | 99.95 | 99.90 |
| Example 19 | 456 | 99.36 | 99.78 |
| Example 20 | 145 | 99.46 | 99.82 |
| Example 21 | 125 | 99.58 | 99.85 |
| Example 22 | 325 | 99.51 | 99.80 |
| Example 23 | 336 | 99.42 | 99.78 |
| Comparative Example 1 | 920 | 97.45 | 99.45 |
| Comparative Example 2 | 721 | 97.32 | 99.58 |
| Comparative Example 3 | 386 | 97.62 | 99.68 |
| Comparative Example 4 | 425 | 97.56 | 99.62 |
| Comparative Example 5 | 856 | 98.24 | 99.68 |
| Comparative Example 6 | 125 | 98.56 | 99.72 |

At least the followings can be seen from Table 2, Table 3, Table 4, Table 5 and FIG. 1:

(1) according to the comparison of Example 1 and Comparative Example 1, the hydrothermal stability of the support was significantly improved and the conversion of α,α-dimethylbenzyl alcohol and the selectivity of isopropylbenzene were significantly improved after adding phosphorus to the support;

(2) according to the comparison of Example 1 and Example 2, when a Pd—Cu composite active component was used, both the conversion of α,α-dimethylbenzyl alcohol and the selectivity of isopropylbenzene were higher than those of a mere Pd active component;

(3) according to the comparison of Example 1 and Example 19, the hydrothermal stability of the support was further improved, and the conversion of α,α-dimethylbenzyl alcohol and the selectivity of isopropylbenzene were further improved after introducing silica to the support;

(4) according to the comparison of Example 1 and Example 20, the conversion of α,α-dimethylbenzyl alcohol and the selectivity of isopropylbenzene were further improved after introducing sulfur to the catalyst;

(5) according to the comparison of Example 3 and Example 6, there was no compressed double-bridge-bonded CO adsorption site on CO-FTIR spectrogram (see FIG. 1); the production quantity of isopropylcyclohexane was significantly reduced, and the conversion of α,α-dimethylbenzyl alcohol and the selectivity of isopropylbenzene were significantly improved after adding S to the catalyst;

(6) according to the respective comparison of Examples 14-17 and Examples 1-13, the production quantity of isopropylcyclohexane was significantly reduced when introducing Cu, S and Si to the catalyst simultaneously.

(7) according to comparison of Example 18 and Example 14, the conversion of α,α-dimethylbenzyl alcohol and the selectivity of isopropylbenzene were significantly improved when a reaction process of two stages of catalyst beds in series was used in relative to the use of one stage of catalyst bed.

(8) all the catalysts in Comparative Examples 3-6 were free of phosphorus, and the conversion of α,α-dimethylbenzyl alcohol was inferior and the selectivity of isopropylbenzene was relatively low.

Stability Test of One Thousand Hours:

Hydrogenation operation was carried out in a fixed bed reactor which was filled with the catalysts produced in Example 14 and Comparative Example 1 respectively. Hydrogenation operation of a hydrocarbon material comprising α,α-dimethylbenzyl alcohol was carried out in a continuous manner.

The operating conditions were as follows:
Reaction temperature: 150° C.
Reaction pressure: 2.0 MPa
Volume space velocity of raw material fresh oil: 1.6 h$^{-1}$
Liquid phase thermal cycle ratio: 4
Hydrogen/α,α-dimethylbenzyl alcohol molar ratio: 8

The average results of 1000 hour evaluation are shown in Table 6.

TABLE 6

Average results of 1000 hour evaluation

| Item | Time hours | Production quantity of isopropylcyclohexane ppm | Conversion of α,α-dimethylbenzyl alcohol % | Selectivity of isopropylbenzene % |
|---|---|---|---|---|
| Catalyst produced in Example 14 | 200 | 16 | 99.75 | 99.90 |
| | 400 | 15 | 99.76 | 99.89 |
| | 600 | 6 | 99.72 | 99.88 |
| | 800 | 6 | 99.78 | 99.88 |
| | 1000 | 0 | 99.79 | 99.90 |
| Catalyst produced in Comparative Example 1 | 200 | 920 | 97.32 | 99.45 |
| | 400 | 854 | 97.28 | 99.56 |
| | 600 | 556 | 97.12 | 99.61 |
| | 800 | 376 | 96.68 | 99.71 |
| | 1000 | 236 | 96.44 | 99.78 |

Stability test of one thousand hours was carried out on the catalysts prepared in Example 14 and Comparative Example 1 respectively. It can be learnt from Table 6 that the catalyst of the present invention not only significantly reduced the production quantity of isopropylcyclohexane in the stage of the initial activity of the catalyst but also remained stable for one thousand hours with the conversion of α,α-dimethylbenzyl alcohol ≥99.72% and the selectivity of isopropylbenzene ≥99.88% in the evaluation of the 1000 hour reaction, as indicated that performance of the catalyst did not undergo a significant change.

II. A Method for Producing Isopropylbenzene from α,α-dimethylbenzyl Alcohol

The method for producing isopropylbenzene from α,α-dimethylbenzyl alcohol of the present invention results in the isopropylbenzene from raw material of a hydrocarbon material comprising α,α-dimethylbenzyl alcohol and hydrogen through a first catalyst bed and a second catalyst bed in series, preferably by the liquid phase thermal cycle process. Relevant examples and comparative examples are listed as below, which however cannot be interpreted as a limitation of the present invention.

Example 1'

1. Catalyst Production
a. Production of the Catalyst of the First Catalyst Bed

1 L of support alumina was mixed with 2000 g of aqueous solution of chloropalladic acid containing 3.0 g of palladium, dried at 110° C. for 8 hours and calcined at 450° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

b. Production of the Catalyst of Second Catalyst Bed

1 L of the support alumina was mixed with 2000 g of aqueous solution of chloropalladic acid-nickel nitrate containing 3.0 g of palladium and 0.3 g of nickel, dried at 110° C. for 8 hours and calcined at 550° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The specific components of the catalyst are shown in Table 2'.

2. Catalyst Evaluation

Hydrogenation operation of the hydrocarbon material comprising α,α-dimethylbenzyl alcohol in Table 1 was carried out in a continuous manner. The material first passed through the first catalyst bed, and then through the second catalyst bed. The catalyst loading volume ratio of the two catalyst beds was 4:1. The operating conditions of the two reactors were as follows:

The First Catalyst Bed:
　Reaction temperature: 150° C.
　Reaction pressure: 1.5 MPa
　Volume space velocity of raw material fresh oil: 2 h$^{-1}$
　Liquid phase thermal cycle ratio: 4
　Hydrogen/raw material fresh oil ratio by volume: 400
The Second Catalyst Bed:
　Reaction temperature: 170° C.
　Reaction pressure: 1.3 MPa
　Hydrogen/raw material fresh oil ratio by volume: 200

The average results of 200 hour evaluation are shown in Table 3'.

Example 2'

1. Catalyst Production
a. Production of the Catalyst of the First Catalyst Bed

1 L of support alumina was mixed with 2000 g of aqueous solution of chloropalladic acid containing 3.0 g of palladium, dried at 110° C. for 8 hours and calcined at 450° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

b. Production of the Catalyst of the Second Catalyst Bed

1 L of the support alumina was mixed with 2000 g of aqueous solution of chloropalladic acid-nickel nitrate-magnesium nitrate containing 3.0 g of palladium, 0.2 g of nickel and 0.1 g of magnesium, dried at 110° C. for 8 hours and calcined at 550° C. for 4 hours to produce a palladium-based catalyst precursor I in an oxidized state. The palladium-based catalyst precursor I in an oxidized state was reduced with hydrogen having a volume space velocity of 100 hour$^{-1}$ for 4 hours at a temperature of 300° C. to produce a palladium-based catalyst. The specific components of the catalyst are shown in Table 2'.

2. Catalyst Evaluation

Hydrogenation operation of the hydrocarbon material comprising α,α-dimethylbenzyl alcohol in Table 1 was carried out in a continuous manner. The material first passed through the first catalyst bed, and then through the second catalyst bed. The catalyst loading volume ratio of the two catalyst beds was 4:1. The operating conditions of the two reactors were as follows:

The First Catalyst Bed:
　Reaction temperature: 150° C.
　Reaction pressure: 1.5 MPa
　Volume space velocity of raw material fresh oil: 2 h$^{-1}$
　Liquid phase thermal cycle ratio: 4
　Hydrogen/raw material fresh oil ratio by volume: 400
The Second Catalyst Bed:
　Reaction temperature: 170° C.
　Reaction pressure: 1.3 MPa
　Hydrogen/raw material fresh oil ratio by volume: 100

The average results of 200 hour evaluation are shown in Table 3'.

Example 3'

1. Catalyst Production
a. Production of the Catalyst of the First Catalyst Bed

1 L of support alumina was mixed with 2000 g of aqueous solution of chloropalladic acid containing 3.0 g of palladium, dried at 110° C. for 8 hours and calcined at 450° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

b. Production of the Catalyst of the Second Catalyst Bed

1 L of the support catalyst was mixed with 2000 g of aqueous solution of chloropalladic acid-copper nitrate containing 3.0 g of palladium and 0.3 g of Cu, dried at 110° C. for 8 hours and calcined at 550° C. for 4 hours to produce a palladium-based catalyst precursor I in an oxidized state. The palladium-based catalyst precursor I in an oxidized state was reduced with hydrogen having a volume space velocity of 100 hour$^{-1}$ for 4 hours at a reduction temperature of 300° C. to produce a palladium-based catalyst. The specific components of the catalyst are shown in Table 2'.

2. Catalyst Evaluation

Hydrogenation operation of the hydrocarbon material comprising α,α-dimethylbenzyl alcohol in Table 1 was carried out in a continuous manner. The material from which heavy components were removed first passed through the first catalyst bed, and then through the second catalyst bed. The catalyst loading volume ratio of the two catalyst beds was 4:1. The operating conditions of the two reactors were as follows:

The First Catalyst Bed:
  Reaction temperature: 150° C.
  Reaction pressure: 1.5 MPa
  Volume space velocity of raw material fresh oil: 2 h$^{-1}$
  Liquid phase thermal cycle ratio: 4
  Hydrogen/raw material fresh oil ratio by volume: 400

The Second Catalyst Bed:
  Reaction temperature: 170° C.
  Reaction pressure: 1.3 MPa
  Hydrogen/raw material fresh oil ratio by volume: 100

The average results of 200 hour evaluation are shown in Table 3'.

Example 4'

The process of Example 2 was repeated, except that in the production of the second catalyst:

1 L of alumina was mixed with 600 of aqueous solution of phosphoric acid containing 60 g of P, dried at 110° C. for 8 hours and calcined at 400° C. for 4 hours to produce a catalyst support.

1 L of the above support was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor in an oxidized state.

The above palladium-based catalyst precursor in an oxidized state was reduced with hydrogen having a volume space velocity of 100 hour$^{-1}$ for 4 hours at a reduction temperature of 35° C. to produce a palladium-based catalyst precursor in a reduced state.

1 L of the above palladium-based catalyst precursor in a reduced state was impregnated with 550 g of cyclohexane solution of tert-nonyl polysulfide containing 0.1 g of sulphur and dried at 110° C. to obtain a catalyst. The major components of the catalyst and the average results of 200 hour evaluation are respectively shown in Table 2' and Table 3'.

Example 5'

The process of Example 2 was repeated, except that in the production of the catalyst in the second stage, specifically:

1 L of alumina was mixed with 600 of aqueous solution of phosphoric acid containing 27 g of P, dried at 110° C. for 8 hours and calcined at 400° C. for 4 hours to produce a catalyst support containing P.

1 L of the above catalyst support containing P was mixed with 600 g of aqueous solution of silica gel having a mass concentration of 5% of $SiO_2$, dried and calcined at 500° C. to obtain a support containing $P/SiO_2$.

1 L of the above support containing $P/SiO_2$ was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor in an oxidized state.

The above palladium-based catalyst precursor in an oxidized state was reduced with hydrogen having a volume space velocity of 100 hour$^{-1}$ for 4 hours at a reduction temperature of 35° C. to produce a palladium-based catalyst precursor in a reduced state.

1 L of the above palladium-based catalyst precursor in a reduced state was impregnated with 550 g of cyclohexane solution of tert-nonyl polysulfide containing 0.1 g of sulphur to obtain a palladium-based catalyst. The major components of the catalyst and the average results of 200 hour evaluation are respectively shown in Table 2' and Table 3'.

Example 6'

The process of Example 5' was repeated, except that in the production of the catalyst in the second stage, specifically:

1 L of alumina was mixed with 600 of aqueous solution of phosphoric acid containing 27 g of P, dried at 110° C. for 8 hours and calcined at 400° C. for 4 hours to produce a catalyst support containing P.

1 L of the above support containing P was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor in an oxidized state.

The above palladium-based catalyst precursor in an oxidized state was reduced with hydrogen having a volume space velocity of 100 hour$^{-1}$ for 4 hours at a reduction temperature of 35° C. to produce a palladium-based catalyst precursor in a reduced state.

1 L of the above palladium-based catalyst precursor in a reduced state was impregnated with 550 g of cyclohexane solution of tert-nonyl polysulfide containing 0.1 g of sulphur to obtain a palladium-based catalyst. The major components of the catalyst and the average results of 200 hour evaluation are respectively shown in Table 2' and Table 3'.

Example 7'

The process of Example 5' was repeated, except that in the production of the catalyst in the second stage, specifically:

1 L of alumina was mixed with 600 of aqueous solution of phosphoric acid containing 27 g of P, dried at 110° C. for 8 hours and calcined at 400° C. for 4 hours to produce a catalyst support containing P.

1 L of the above support containing P was mixed with 2000 g of aqueous solution of chloropalladic acid-copper nitrate containing 3.0 g of palladium and 1.0 g of copper, dried at 110° C. for 8 hours and calcined at 500° C. for 4 hours to produce a palladium-based catalyst precursor in an oxidized state.

The above palladium-based catalyst precursor in an oxidized state was reduced with hydrogen having a volume space velocity of 100 hour$^{-1}$ for 4 hours at a reduction temperature of 35° C. to produce a palladium-based catalyst.

The major components of the catalyst and the average results of 200 hour evaluation are respectively shown in Table 2' and Table 3'.

Example 8'

The process of Example 5' was repeated, except that in the production of the catalyst in the second stage, specifically:

1 L of alumina was mixed with 600 g of aqueous solution of phosphoric acid containing 27 g of P, dried at 110° C. for 8 hours and calcined at 400° C. for 4 hours to produce a catalyst support containing P.

1 L of the above support containing P was mixed with 2000 g of aqueous solution of chloropalladic acid containing 3.0 g of palladium, dried at 110° C. for 8 hours and calcined at 500° C. for 4 hours to produce a palladium-based catalyst precursor in an oxidized state.

The above palladium-based catalyst precursor in an oxidized state was reduced with hydrogen having a volume space velocity of 100 hour$^{-1}$ for 4 hours at a reduction temperature of 35° C. to produce a palladium-based catalyst. The major components of the catalyst and the average results of 200 hour evaluation are respectively shown in Table 2' and Table 3'.

Comparative Example 1'

1. Catalyst Production

1 L of support alumina was mixed with 2000 g of aqueous solution of chloropalladic acid-nickel nitrate containing 3.0 g of palladium and 0.3 g of nickel, dried at 110° C. for 8 hours and calcined at 550° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

2. Catalyst Evaluation

Hydrogenation operation of the hydrocarbon material comprising α,α-dimethylbenzyl alcohol in Table 1 was carried out in a continuous manner. The material from which heavy components were removed only passed through one catalyst bed. The catalyst loading of the one catalyst bed was the same as that of two catalyst beds when employed. The specific operating conditions were as follows:

Reaction temperature: 150° C.
Reaction pressure: 1.50 MPa
Volume space velocity of raw material fresh oil: 2 h$^{-1}$
Liquid phase thermal cycle ratio: 4
Hydrogen/raw material fresh oil ratio by volume: 400

The average results of 200 hour evaluation are shown in Table 3'.

Comparative Example 2'

1. Catalyst Production

1 L of support alumina was mixed with 2000 g of aqueous solution of chloropalladic acid containing 3.0 g of palladium, dried at 110° C. for 8 hours and calcined at 450° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

2. Catalyst Evaluation

Hydrogenation operation of the hydrocarbon material comprising α,α-dimethylbenzyl alcohol in Table 1 was carried out in a continuous manner. The material from which heavy components were removed only passed through one catalyst bed. The catalyst loading of the one catalyst bed was the same as that of two catalyst beds when employed. The specific operating conditions were as follows:

Reaction temperature: 150° C.
Reaction pressure: 1.50 MPa
Volume space velocity of raw material fresh oil: 2 h$^{-1}$
Liquid phase thermal cycle ratio: 4
Hydrogen/raw material fresh oil ratio by volume: 400

The average results of 200 hour evaluation are shown in Table 3'.

Comparative Example 3'

1. Catalyst Production a. Production of the Catalyst of the First Catalyst Bed

1 L of support alumina was mixed with 2000 g of aqueous solution of chloropalladic acid containing 3.0 g of palladium, dried at 110° C. for 8 hours and calcined at 450° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

b. Production of the Catalyst of the Second Catalyst Bed

1 L of support alumina was mixed with 2000 g of aqueous solution of chloropalladic acid-nickel nitrate containing 3.0 g of palladium and 0.3 g of nickel, dried at 110° C. for 8 hours and calcined at 550° C. for 4 hours to produce a palladium-based catalyst precursor I in an oxidized state. The above palladium-based catalyst precursor I in an oxidized state was reduced with hydrogen having a volume space velocity of 100 hour$^{-1}$ for 4 hours at a reduction temperature of 300° C. to produce a palladium-based catalyst. The major components of the catalyst are shown in Table 2'.

2. Catalyst Evaluation

Hydrogenation operation of the hydrocarbon material comprising α,α-dimethylbenzyl alcohol in Table 1 was carried out in a continuous manner. The material first passed through the first catalyst bed, and then through the second catalyst bed. The catalyst loading volume ratio of the two catalyst beds was 1:4. The operating conditions of the two reactors were as follows:

The First Catalyst Bed:
Reaction temperature: 150° C.
Reaction pressure: 1.50 MPa
Volume space velocity of raw material fresh oil: 2 h$^{-1}$
Liquid phase thermal cycle ratio: 4
Hydrogen/raw material fresh oil ratio by volume: 400

The Second Catalyst Bed:
Reaction temperature: 170° C.
Reaction pressure: 1.3 MPa
Hydrogen/raw material fresh oil ratio by volume: 400

The average results of 200 hour evaluation are shown in Table 3'.

Comparative Example 4'

Production of the Catalyst in Example 1' was Repeated, Except that in the Catalyst Evaluation:

Hydrogenation operation of the hydrocarbon material comprising α,α-dimethylbenzyl alcohol in Table 1 was carried out in a continuous manner.

The material first passed through the first catalyst bed, and then through the second catalyst bed. The catalyst loading volume ratio of the two catalyst beds was 4:1. The operating conditions of the two reactors were as follows:

The First Catalyst Bed:
- Reaction temperature: 150° C.
- Reaction pressure: 1.50 MPa
- Volume space velocity of raw material fresh oil: 2 h$^{-1}$
- Liquid phase thermal cycle ratio: 0
- Hydrogen/raw material fresh oil ratio by volume: 400

The Second Catalyst Bed:
- Reaction temperature: 170° C.
- Reaction pressure: 1.3 MPa
- Hydrogen/raw material fresh oil ratio by volume: 200

The average results of 200 hour evaluation are shown in Table 3'.

TABLE 2'

| Number | Item | Al$_2$O$_3$ g/L | Pd g/L | Metal auxiliary g/L | P g/L | S g/L | SiO$_2$ g/L |
|---|---|---|---|---|---|---|---|
| Example 1' | First stage catalyst | 568 | 2.87 | 0 | 0 | 0 | 0 |
| | Second stage catalyst | 556 | 2.79 | Ni-0.34 | 0 | 0 | 0 |
| Example 2' | First stage catalyst | 554 | 2.78 | 0 | 0 | 0 | 0 |
| | Second stage catalyst | 556 | 2.83 | Ni-0.24/Mg-0.09 | 0 | 0 | 0 |
| Example 3' | First stage catalyst | 558 | 2.81 | 0 | 0 | 0 | 0 |
| | Second stage catalyst | 561 | 2.79 | Cu-0.28 | 0 | 0 | 0 |
| Example 4' | First stage catalyst | 558 | 2.91 | 0 | 0 | 0 | 0 |
| | Second stage catalyst | 552 | 2.86 | Cu-0.89 | 56.32 | 0.083 | 0 |
| Example 5' | First stage catalyst | 558 | 2.82 | 0 | 0 | 0 | 0 |
| | Second stage catalyst | 552 | 2.78 | Cu-0.90 | 25.23 | 0.080 | 26 |
| Example 6' | First stage catalyst | 558 | 2.82 | 0 | 0 | 0 | 0 |
| | Second stage catalyst | 552 | 2.78 | Cu-0.90 | 25.23 | 0.080 | 0 |
| Example 7' | First stage catalyst | 558 | 2.82 | 0 | 0 | 0 | 0 |
| | Second stage catalyst | 552 | 2.78 | Cu-0.90 | 25.23 | 0 | 0 |
| Example 8' | First stage catalyst | 554 | 2.78 | 0 | 0 | 0 | 0 |
| | Second stage catalyst | 554 | 2.78 | 0 | 25.23 | 0 | 0 |
| Comparative Example 1' | Single stage catalyst | 560 | 2.84 | Ni-0.32 | 0 | 0 | 0 |
| Comparative Example 2' | Single stage catalyst | 563 | 2.76 | 0 | 0 | 0 | 0 |
| Comparative Example 3' | First stage catalyst | 551 | 2.77 | 0 | 0 | 0 | 0 |
| | Second stage catalyst | 548 | 2.84 | Ni-0.33 | 0 | 0 | 0 |
| Comparative Example 4' | First stage catalyst | 568 | 2.87 | 0 | 0 | 0 | 0 |
| | Second stage catalyst | 556 | 2.79 | Ni-0.34 | 0 | 0 | 0 |

TABLE 3'

| Item | Content of isopropylbenzene hydroperoxide in hydrogenation product ppm | Content of α-methylstyrene in hydrogenation product ppm | Content of dimerized isopropylbenzene ppm | Content of α,α-dimethylbenzyl alcohol in hydrogenation product ppm | Selectivity of isopropylbenzene % |
|---|---|---|---|---|---|
| Example 1' | 0 | 12 | 86 | 186 | 99.82 |
| Example 2' | 0 | 8.6 | 67 | 146 | 99.87 |
| Example 3' | 0 | 5.8 | 78 | 85 | 99.83 |
| Example 4' | 0 | 3.2 | 51 | 54 | 99.92 |
| Example 5' | 0 | 2.5 | 48 | 32 | 99.95 |
| Example 6' | 0 | 4.8 | 58 | 68 | 99.90 |
| Example 7' | 0 | 5.1 | 62 | 71 | 99.88 |
| Example 8' | 0 | 5.3 | 66 | 75 | 99.86 |
| Comparative Example 1' | 18 | 350 | 412 | 46520 | 99.72 |
| Comparative Example 2' | 22 | 467 | 426 | 57368 | 99.64 |
| Comparative Example 3' | 0 | 12 | 245 | 4876 | 99.69 |
| Comparative Example 4' | 0 | 356 | 3250 | 123 | 99.12 |

It can be seen from Table 2' and Table 3':

(1) According to the respective comparison between Comparative Examples 1'-2' and Example 1', and Example 3', in which both Comparative Examples 1'-2' employed a single catalyst bed filled with the same amount of catalyst, it can be seen that the content of isopropylbenzene hydroperoxide, the content of α-methylstyrene, the content of dimerized isopropyl benzene and the content of α,α-dimethylbenzyl alcohol in the products of Comparative Examples 1'-2' were all higher than those in the examples, particularly the content of α,α-dimethylbenzyl alcohol. The above indicates that the method according to the present invention can achieve a high conversion to α,α-dimethylbenzyl alcohol. (2) According to the comparison between Comparative Examples 3' and Example 1', in which the catalyst loading in the first catalyst bed in Comparative Example 3' was lower than that of the second catalyst bed, it can be seen that the content of dimerized isopropyl benzene and the content of α,α-dimethylbenzyl alcohol in the product of Comparative Examples 3' were significantly higher.

(3) According to the comparison between Examples 5' and Example 3', when phosphorus, silica and sulfur were introduced to the second catalyst simultaneously, the content of isopropylbenzene hydroperoxide, the content of α-methylstyrene, the content of dimerized isopropyl benzene and the content of α,α-dimethylbenzyl alcohol in the product of Examples 5' were all lower than those in Example 3'.

(4) According to the comparison between Examples 6' and Example 5', when only phosphorus and sulfur were introduced to the second catalyst, the content of isopropylbenzene hydroperoxide, the content of α-methylstyrene, the content of dimerized isopropyl benzene and the content of α,α-dimethylbenzyl alcohol in the product of Examples 6' were all higher than those in Example 5'.

(5) According to the comparison between Example 7' and Example 5', when only phosphorus was introduced to the second catalyst, the content of isopropylbenzene hydroperoxide, the content of α-methylstyrene, the content of dimerized isopropyl benzene and the content of α,α-dimethylbenzyl alcohol in the product of Example 7' were all higher than those in Example 5'.

(6) According to the comparison between Examples 8' and Example 7', when only phosphorus was introduced to the second catalyst, the content of isopropylbenzene hydroperoxide, the content of α-methylstyrene, the content of dimerized isopropyl benzene and the content of α,α-dimethylbenzyl alcohol in the product of Examples 8' were all higher than those in Example 7'.

(7) According to the comparison between Comparative Example 4' and Example 1', in which the liquid phase thermal cycle ratio of the first catalyst bed in the operating conditions of the reactor of Comparative Examples 4' was 0, it can be seen that the content of dimerized isopropyl benzene in the product of Comparative Examples 4' was significantly higher and the selectivity of isopropylbenzene was significantly lowered.

The invention claimed is:

1. A catalyst for producing isopropylbenzene from α,α-dimethylbenzyl alcohol, comprising a support and an active component supported on the support, wherein the support comprises a support substrate and a modifying auxiliary component supported on the support substrate,
wherein the active component includes metal palladium and/or an oxide thereof, and the modifying auxiliary component includes phosphorus and/or an oxide thereof,
wherein the support substrate is not silica, and said modifying auxiliary component further includes silica, and
wherein a molar ratio of the silicon to phosphorus in the catalyst based on the element is ≤10.

2. The catalyst according to claim 1, wherein a content of the metal palladium and/or oxide thereof in the catalyst is 0.01-5 wt %, based on a content of the element palladium, and/or
the metal palladium has a dispersity of 5-10%.

3. The catalyst according to claim 2, wherein the active component further includes an active auxiliary metal and/or an oxide thereof; the active auxiliary metal is at least one selected from the group consisting of metal copper, metal zinc, metal cobalt, metal tin, metal nickel and metal silver;
and a content of the active auxiliary metal and/or oxide thereof in the catalyst is 0.0001-0.2 wt %, based on a content of the auxiliary metal element therein.

4. The catalyst according to claim 1, wherein a content of the modifying auxiliary component in the catalyst is 0.2-20 wt %, based on a content of element phosphorus.

5. The catalyst according to claim 1, wherein the support substrate is at least one selected from the group consisting of alumina and activated carbon, and/or the support substrate has a pore size of 10-25 nm and a specific surface area of 50-180 m$^2$/g.

6. The catalyst according to claim 1, wherein the catalyst further includes a co-catalyst of a sulfur-containing compound which is at least one selected from the group consisting of tert-nonyl polysulfides, tert-butyl polysulfides, thiophenes and dimethyl disulfides; and
a content of the co-catalyst in the catalyst is >0-1 wt %, based on an amount of element sulfur.

7. The catalyst according to claim 1, wherein a content of silica in the catalyst is >0-60 wt %.

8. The catalyst according to claim 1, wherein the molar ratio of silicon to phosphorus in the catalyst based on the element is ≤4, wherein, a content of the modifying auxiliary component phosphorus and/or oxide thereof in the catalyst is 0.2-20 wt %, wherein the content of phosphorus and/or oxide thereof is based on a content of element phosphorus therein, and a silica content in the catalyst is >0-60 wt %.

9. The catalyst according to claim 1, wherein the molar ratio of silicon to phosphorus in the catalyst based on the element is ≤7.60.

10. A method for producing the catalyst according to claim 1, comprising the following steps:
Step 1: an aqueous solution of a phosphorus-containing compound is mixed with a support substrate, dried and calcined to obtain a phosphorus-containing support;
Step 1': the phosphorus-containing support is mixed with an aqueous solution of silica gel, dried and calcined to obtain a support containing phosphorus and silicon;
Step 2: the support containing phosphorus and silicon is added to a solution of a palladium-containing compound, dried and calcined to obtain a catalyst precursor in an oxidized state;
Step 3: the catalyst precursor in an oxidized state is subjected to a reduction treatment to obtain the catalyst.

11. The method according to claim 10, wherein the support substrate is at least one selected from the group consisting of alumina and activated carbon, and/or
the palladium-containing compound is at least one selected from the group consisting of palladium chloride, palladium nitrate and chloropalladic acid, and/or
the phosphorus-containing compound is at least one selected from the group consisting of phosphoric acid, potassium dihydrogen phosphate, phosphorous acid, calcium phosphate and ammonium hydrogen phosphate, and/or the solution in step 2 further comprises a compound containing an active auxiliary metal which is at least one selected from the group consisting of active auxiliary metal chlorides, compounds of active auxiliary metal nitrates and compounds of active auxiliary metal acetates; wherein the active auxiliary metal is at least one selected from the group consisting of metal copper, metal zinc, metal cobalt, metal tin, metal nickel and metal silver.

12. The method according to claim 10, wherein in step 1 and step 2, a calcining temperature is 400-700° C., and/or in step 3, a reduction treatment is carried out with hydrogen; a reduction temperature is 40-300° C.; and a volume space velocity of hydrogen is 50-500h$^{-1}$.

13. The method according to claim 10, wherein the method further comprises step 4:

Step 4: the catalyst according to step 3 is added to a co-catalyst-containing solution and dried to obtain a further catalyst, wherein the co-catalyst is a sulfur-containing compound.

14. The method according to claim 10, wherein, based on 1 L of the support substrate, an amount of the palladium-containing compound is 0.06 g/L-30 g/L, based on an amount of element palladium therein, and/or an amount of the compound containing an active auxiliary metal is 0.0006 g/L-1.2 g/L, based on an amount of the element of the active auxiliary metal therein, and/or an amount of the phosphorus-containing compound is 2 g/L-100 g/L, based on an amount of element phosphorus therein, and/or an amount of the co-catalyst is 0.0001 g/L-3 g/L, based on an amount of element sulfur therein, and/or an amount of silica gel is 6-300 g/L, based on an amount of silica therein.

15. A method for producing isopropylbenzene from α,α-dimethylbenzyl alcohol, wherein the method comprises: bringing a α,α-dimethylbenzyl alcohol-containing raw material in contact with hydrogen to react in the presence of the catalyst according to claim 1 to obtain isopropylbenzene.

16. The method according to claim 15, wherein the raw material comprises a hydrocarbon material comprising α,α-dimethylbenzyl alcohol, wherein the hydrocarbon material optionally comprises isopropylbenzene, acetophenone, α-methylstyrene, dimerized isopropyl benzene, and isopropylbenzene hydroperoxide; and/or the method is a liquid phase thermal cycle process.

17. The method according to claim 16, wherein a pressure is 0.1-4.0 MPa, a temperature is 130-220° C., a liquid hourly space velocity is 1-20 h$^{-1}$, and a molar ratio of hydrogen to α,α-dimethylbenzyl alcohol is >4.

18. The method according to claim 15, comprising obtaining the isopropylbenzene from a raw material of a hydrocarbon material comprising α,α-dimethylbenzyl alcohol and hydrogen through a first catalyst bed and a second catalyst bed in series, by a liquid phase thermal cycle process;

wherein, a catalyst loading of the first catalyst bed is greater than or equal to that of the second catalyst bed; an inlet temperature of the first catalyst bed is not higher than an inlet temperature of the second catalyst bed; the first catalyst bed has a reaction temperature of 130-190° C., a reaction pressure of 0.1-5MPa, and a liquid hourly space velocity of 1.0-20 h$^{-1}$, and/or the second catalyst bed has a reaction temperature of 150-230° C., a reaction pressure of 0.1-5 MPa, and a liquid phase volume space velocity of 2.0-10 h$^{-1}$, a liquid phase thermal cycle ratio of the first catalyst bed is 1-10; and a liquid phase thermal cycle ratio of the second catalyst bed is 0-2.

19. The method according to claim 18, wherein, in the first catalyst bed, a ratio by volume of hydrogen to a liquid phase is 300-1000, and/or in the second catalyst bed, a ratio by volume of hydrogen to a liquid phase is 100-800.

20. The method according to claim 18, wherein, a first catalyst of the first catalyst bed and/or a second catalyst of the second catalyst bed is the catalyst according to claim 1, the second catalyst optionally further comprising a metal auxiliary and/or an oxide thereof, the metal auxiliary being at least one selected from the group consisting of Fe, Co, Ni, Ca, Mg and Cu.

21. A method for producing propylene oxide, wherein the method comprises:

step 1: bringing a α,α-dimethylbenzyl alcohol-containing raw material in contact with hydrogen to react in the presence of the catalyst according to claim 1 to obtain isopropylbenzene, step 2: obtaining isopropylbenzene hydroperoxide by oxidation of the isopropylbenzene from step 1;

step 3: obtaining propylene oxide and α,α-dimethylbenzyl alcohol from a reaction of propylene and the isopropylbenzene hydroperoxide from step 2; and step 4: separating the propylene oxide from the α,α-dimethylbenzyl alcohol obtained in step 3.

* * * * *